(12) United States Patent
Bommagani et al.

(10) Patent No.: US 10,512,608 B2
(45) Date of Patent: Dec. 24, 2019

(54) NANOPARTICULATE COMPOSITION

(71) Applicant: SUN PHARMA ADVANCED RESEARCH COMPANY LTD., Mumbai (IN)

(72) Inventors: Madhusudhan Bommagani, Baroda (IN); Subhas Balaram Bhowmick, Baroda (IN); Prashant Kane, Baroda (IN); Vaibhav Dubey, Baroda (IN)

(73) Assignee: SUN PHARMA ADVANCED RESEARCH COMPANY LTD., Mumbai (IN)

( * ) Notice: Subject to any disclaimer, the term of this patent is extended or adjusted under 35 U.S.C. 154(b) by 0 days.

(21) Appl. No.: 15/552,966

(22) PCT Filed: Feb. 25, 2016

(86) PCT No.: PCT/IN2016/050068
§ 371 (c)(1),
(2) Date: Aug. 23, 2017

(87) PCT Pub. No.: WO2016/135754
PCT Pub. Date: Sep. 1, 2016

(65) Prior Publication Data
US 2018/0036243 A1    Feb. 8, 2018

(30) Foreign Application Priority Data
Feb. 25, 2015 (IN) .......................... 623/MUM/2015

(51) Int. Cl.
| A61K 9/14 | (2006.01) |
| A61K 31/65 | (2006.01) |
| A61K 9/00 | (2006.01) |
| A61K 9/06 | (2006.01) |
| A61K 9/10 | (2006.01) |
| A61K 9/12 | (2006.01) |
| A61K 47/14 | (2017.01) |

(52) U.S. Cl.
CPC ............ *A61K 9/146* (2013.01); *A61K 9/0014* (2013.01); *A61K 9/06* (2013.01); *A61K 9/10* (2013.01); *A61K 9/122* (2013.01); *A61K 31/65* (2013.01); *A61K 47/14* (2013.01); *Y02A 50/473* (2018.01)

(58) Field of Classification Search
CPC ........ A61K 9/0014; A61K 9/10; A61K 9/146; A61K 9/06; A61K 31/65; A61K 9/122; A61K 47/14
See application file for complete search history.

(56) References Cited

U.S. PATENT DOCUMENTS

| 5,122,519 A | 6/1992 | Ritter |
| 8,518,376 B2 | 8/2013 | Tamarkin et al. |
| 8,784,852 B2 | 7/2014 | Kunin |
| 8,865,139 B1 | 10/2014 | Tamarkin et al. |
| 8,871,184 B2 | 10/2014 | Tamarkin et al. |
| 8,945,516 B2 | 2/2015 | Tamarkin et al. |
| 8,992,896 B2 | 3/2015 | Tamarkin et al. |
| 9,539,266 B2 | 1/2017 | Mansouri |
| 9,549,898 B2 | 1/2017 | Tamarkin et al. |
| 9,675,700 B2 | 6/2017 | Tamarkin et al. |
| 9,763,968 B2 | 9/2017 | Sinko et al. |
| 2004/0115134 A1 | 6/2004 | Merisko-Liversidge |
| 2005/0019412 A1 | 1/2005 | Bosch et al. |
| 2007/0259013 A1* | 11/2007 | Shevachman ........ A61K 9/0014 424/401 |
| 2007/0292461 A1* | 12/2007 | Tamarkin .................. A61K 8/86 424/401 |
| 2008/0188445 A1 | 8/2008 | Muldoon et al. |
| 2008/0188446 A1 | 8/2008 | Muldoon et al. |
| 2008/0220075 A1 | 9/2008 | Merisko-Liversidge et al. |
| 2010/0221245 A1 | 9/2010 | Kunin |
| 2011/0165251 A1* | 7/2011 | Bosch .................. A61K 9/0095 424/489 |
| 2012/0087872 A1 | 4/2012 | Tamarkin et al. |
| 2013/0011342 A1 | 1/2013 | Tamarkin et al. |
| 2013/0028850 A1 | 1/2013 | Tamarkin et al. |
| 2013/0064777 A1 | 3/2013 | Tamarkin et al. |

(Continued)

FOREIGN PATENT DOCUMENTS

| WO | 2004/006959 A1 | 1/2004 |
| WO | 2005079746 A1 | 9/2005 |

(Continued)

OTHER PUBLICATIONS

Minocycline entry of PubChem 2018 (Year: 2018).*
International Search Report for PCT/IN2016/050068 dated Jul. 14, 2016 [PCT/ISA/210].
Written Opinion for PCT/IN2016/050068 dated Jul. 14, 2016 [PCT/ISA/237].

*Primary Examiner* — Mina Haghighatian
(74) *Attorney, Agent, or Firm* — Sughrue Mion, PLLC

(57) ABSTRACT

The present invention relates to a nanoparticulate topical composition comprising (i) nanoparticles of a water soluble and water susceptible active ingredient or its pharmaceutically acceptable salt, having a particle size distribution such that 90% of the particles are less than 1000 nm, (ii) one or more wetting agent and (iii) a non-aqueous liquid vehicle, wherein the composition is free of water.

The present invention also relates to a method of treating acne, rosacea, impetigo or a skin disease caused by a bacteria, by topical application of a nanoparticulate topical composition comprising nanoparticles of a water soluble and water susceptible active ingredient or its pharmaceutically acceptable salt, having a particle size distribution such that 90% of the particles are less than 1000 nm.

8 Claims, 1 Drawing Sheet

(56) References Cited

U.S. PATENT DOCUMENTS

| | | |
|---|---|---|
| 2013/0225536 A1 | 8/2013 | Tamarkin et al. |
| 2014/0328770 A1 | 11/2014 | Tamarkin et al. |
| 2015/0056149 A1 | 2/2015 | Tamarkin et al. |
| 2015/0190409 A1 | 7/2015 | Tamarkin et al. |
| 2015/0196570 A1 | 7/2015 | Tamarkin et al. |
| 2016/0158261 A1 | 6/2016 | Friedman et al. |
| 2016/0213757 A1 | 7/2016 | Edelson et al. |
| 2016/0287614 A1 | 10/2016 | Mandhare et al. |
| 2016/0346294 A1 | 12/2016 | Sengupta et al. |
| 2017/0182071 A1 | 6/2017 | Salman et al. |
| 2017/0189427 A1 | 7/2017 | Mansouri |

FOREIGN PATENT DOCUMENTS

| | | |
|---|---|---|
| WO | 2008097850 A1 | 8/2008 |
| WO | 2008097851 A1 | 8/2008 |
| WO | 2010041141 A2 | 4/2010 |
| WO | 2010125470 A2 | 11/2010 |
| WO | 2011039637 A2 | 4/2011 |
| WO | 2011039638 A2 | 4/2011 |
| WO | 2011064631 A1 | 6/2011 |
| WO | 2015114666 A2 | 8/2015 |

\* cited by examiner

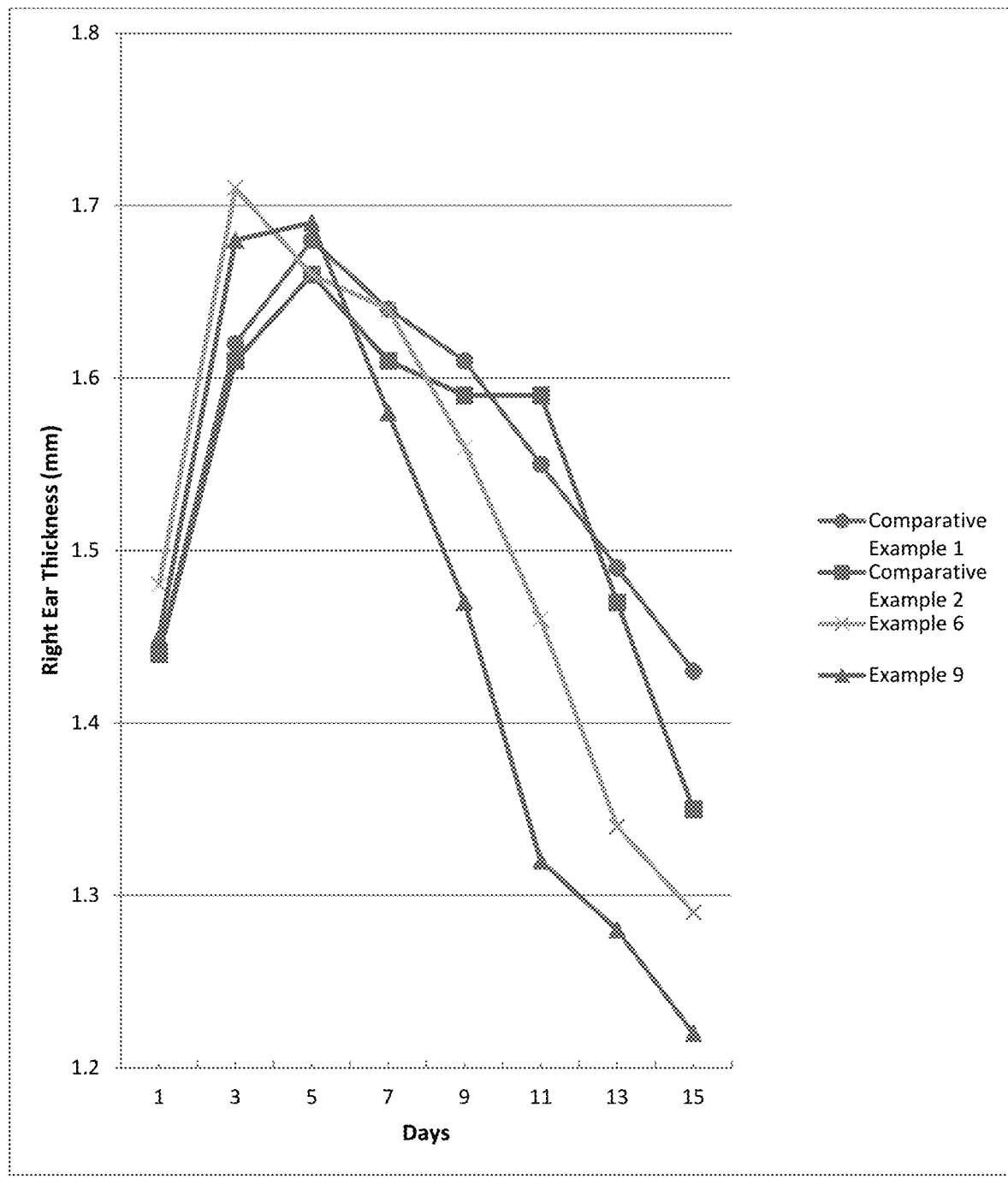

NANOPARTICULATE COMPOSITION

CROSS REFERENCE TO RELATED APPLICATIONS

This application is a National Stage of International Application No. PCT/IN2016/050068 filed Feb. 25, 2016, claiming priority based on Indian Patent Application No. 623/MUM/2015, filed Feb. 25, 2015, the contents of all of which are incorporated herein by reference in their entirety.

FIELD OF THE INVENTION

The present invention relates to a nanoparticulate topical composition comprising
i. nanoparticles of a water soluble and water susceptible active ingredient or its pharmaceutically acceptable salt, having a particle size distribution such that 90% of the particles are less than 1000 nm.
ii. one or more wetting agent and
iii. a non-aqueous liquid vehicle
wherein the composition is free of water.

The present invention also relates to a method of treating acne, rosacea, impetigo or a skin disease caused by bacteria, by topical application of a nanoparticulate topical composition comprising nanoparticles of a water soluble and water susceptible active ingredient or its pharmaceutically acceptable salt, having a particle size distribution such that 90% of the particles are less than 1000 nm.

BACKGROUND OF THE INVENTION

Water soluble active ingredients that are susceptible to degradation in the presence of water are difficult to formulate. A major challenge in the development of topical compositions of these water soluble and water susceptible active ingredients lies in maintaining their physico-chemical stability. This is because such drugs are unstable in solution form and are sensitive to water, light, moisture and protic solvents. Further, the oxidative processes are also responsible for destabilizing many of these active agents in formulations leading to physico-chemical instability.

Since the drugs are susceptible to hydrolysis, topical compositions comprising aqueous phase or polar solvent are not feasible due to drug instability. Further, in case of non-aqueous composition, the penetration of a water soluble active ingredient becomes a major concern in that the composition do not show proper therapeutic effect upon topical application, due to lack of absorption or penetration.

There remains a medical need for a stable, commercially feasible, easy to manufacture and easy to use topical composition of a water soluble, water susceptible active drug which on one hand is physically and chemically stable for the duration of its shelf life and on the other hand show optimum drug bio-availability and efficacy upon topical application. The present invention fulfills this need. The present inventors have surprisingly found a solution to the aforesaid problems by providing a nanoparticulate topical composition of a water soluble and water susceptible active ingredient which is physically and chemically stable. It was surprisingly observed that in the nanoparticulate topical composition developed by the present inventors, the active ingredient remained stable inspite of undergoing nanosizing, which otherwise result in formation of impurities. The present inventors have also discovered that compositions containing nanoparticles of minocycline or its pharmaceutically acceptable salts, a water soluble and water susceptible active agent, provide an improved efficacy.

SUMMARY OF THE INVENTION

The present invention provides a nanoparticulate topical composition comprising
i. nanoparticles of a water soluble and water susceptible active ingredient or its pharmaceutically acceptable salt, having a particle size distribution such that 90% of the particles are less than 1000 nm.
ii. one or more wetting agent and
iii. a non-aqueous liquid vehicle
wherein the composition is free of water.

The present invention further provides a method of treating acne, rosacea, impetigo or a skin disease caused by bacteria, by topical application of a nanoparticulate topical composition comprising nanoparticles of minocycline or its pharmaceutically acceptable salt, having a particle size distribution such that 90% of the particles are less than 1000 nm in a non-aqueous liquid vehicle.

DESCRIPTION OF THE FIGURES

FIG. 1: It illustrates a graph showing right ear thickness at various time points from day 1 to day 14 for various treatment groups i.e. nanoparticulate topical composition of Example 6 (-X-), nanoparticulate topical composition of Example 9 (-▲-); topical composition as per comparative example 1 (-●-) and topical compositions as per comparative examples 2 (-■-).

DESCRIPTION OF THE INVENTION

The term "nanoparticle" or "nanoparticulate" as used herein refers to the solid particles of active ingredient having a particle size in nanometer (nm), such that 90% of the particles ($D_{90}$) have a size less than 1000 nanometers (nms), i.e. $D_{90}$ is less than 1000 nanometers (nm). The solid particles consist of the active ingredient in that the solid particles are devoid of any other excipient which may either encapsulate the active ingredient, or embed the active ingredient within itself for example liposomally entrapped particle, or active ingredients entrapped in a porous structure of an excipient such as calcium or silica or any polymer. It may be noted that the solid particles may include excipients adsorbed onto its surface, such as for example wetting agents, surfactants or surface stabilizers, which are adsorbed onto the surface of the active ingredient and there is no composite particle formed thereof.

The term "nanoparticulate composition" or "nanosuspension" as used herein refers to composition comprising the solid particles of active ingredient having particle size in nanometers, such that 90% of the particles have a size less than 1000 nm, i.e. $D_{90}$ is less than 1000 nms.

The particle size is expressed in terms of particle size distribution including values of $D_{90}$, $D_{50}$ and $D_{10}$, as measured by techniques such as laser light diffraction technique, photon correlation spectroscopy; sedimentation field flow fractionation, or disk centrifugation.

The phrase $D_{90}$ of less than Y nm—as used herein means that particle size distribution is such that at least 90% of the particles have a size/diameter of less than Y nm when measured by conventional techniques, such as laser light diffraction technique, photon correlation spectroscopy; sedimentation field flow fractionation, or disk centrifugation.

The phrase $D_{50}$ of less than X nm—as used herein means that particle size distribution is such that at least 50% of the particles have a size/diameter of less than X nm when measured by conventional techniques, such as laser light diffraction technique, photon correlation spectroscopy; sedimentation field flow fractionation, or disk centrifugation.

The phrase $D_{10}$ of less than Z nm—as used herein means that particle size distribution is such that at least 10% of the particles have a size/diameter of less than Z nm when measured by conventional techniques.

The term "non-aqueous" as used herein means free of added water. According to one or more embodiments, the nanoparticulate topical compositions or non-aqueous nanosuspensions of the present invention are free of water. The term "liquid vehicle" as used herein includes a vehicle that can be poured from one container to another container or a vehicle can be sprayed or can form foam or any semisolid vehicle that can be squeezed out from a flexible container such as an ointments tube. In preferred embodiments, it includes a topical vehicle comprising pharmaceutically acceptable excipients employed in formulating topical dosage forms such as a gel, foam, an ointment, a suspension, an aerosol, a spray, a cream, a lotion.

The term "water soluble active ingredient" as used herein refers to therapeutically active drug substances that have a solubility greater then 1 mg per ml in water. The term "water susceptible" as used herein refers to water soluble active ingredient that chemically degrades in the presence of water, either instantaneously or at a rate such that it does not remain within its specifications such as those specified as per ICH guidelines, over a shelf life period of up to 1 year. The term "water soluble, and water-susceptible active ingredient" as used herein refers to therapeutically active drug substances that have a solubility greater than 1 mg per ml in water and that typically chemically degrades in the presence of water instantaneously or at a rate such that it does not remain within its specifications over a shelf life period of up to 1 year.

According to one embodiment of the present invention, there is provided a nanoparticulate topical composition comprising
  i. nanoparticles of a water soluble, water-susceptible active ingredient or its pharmaceutically acceptable salt, having a particle size distribution such that 90% of the particles are less than 1000 nm.
  ii. one or more wetting agent and
  iii. a non-aqueous liquid vehicle
wherein the composition is free of water.

According to another embodiment of the present invention, there is provided a non-aqueous nanosuspension comprising
  i. nanoparticles of a water soluble, water-susceptible active ingredient or its pharmaceutically acceptable salt, having a particle size distribution such that 90% of the particles are less than 1000 nm.
  ii. one or more wetting agent and
  iii. a non-aqueous liquid vehicle
wherein the nanosuspension is free of water.

According to another embodiment of the present invention, there is provided a method of treating acne, rosacea, impetigo or a skin disease caused by bacteria, by topical application of a non-aqueous nanoparticulate topical composition comprising nanoparticles of a water soluble, water-susceptible active ingredient or its pharmaceutically acceptable salt, having a particle size distribution such that 90% of the particles are less than 1000 nm.

In one or more embodiments according to the present invention, the nanoparticulate topical composition including the non-aqueous nanosuspension comprises nanoparticles of water soluble active ingredient or its salt, having a particle size distribution such that 90% of the particles are less than 1000 nm i.e. $D_{90}$ is less than 1000 nms. In preferred embodiments, the nanoparticles have a particle size distribution such that $D_{90}$ is less than 1000 nms and ($D_{50}$) is less than 800 nm. Preferably, the nanoparticles of water soluble active ingredient or its salts have a particle size distribution such that $D_{90}$ is less than 700 nm, $D_{50}$ is less than 500 nm, and $D_{10}$ is less than 300 nms. Suitably, according to the present invention, laser light diffraction technique is preferably used for the determination of particle size and its distribution. The laser light diffraction technique used for the determination of particle size and its distribution is based on the analysis of the diffraction pattern produced when particles are exposed to a beam of monochromatic light. Suitably, the instruments based on this technique that can be preferably used include Malvern Mastersizer or Malvern Zetasizer.

Suitably, the water soluble active ingredient that may be used according to the present invention includes water soluble active ingredients that are water susceptible. The active agent may be in the form of a pharmaceutically acceptable salt or free base or mixtures thereof. The active ingredient, either in free form or as its salt form, is susceptible to degradation in the presence of water. In one or more embodiment, nanoparticulate topical composition of the present invention includes topically effective water soluble and water susceptible active ingredients.

In certain preferred embodiments, the water soluble, water-susceptible active agent is a tetracycline antibiotic. In one or more embodiments, the tetracycline antibiotic is tetracycline, minocycline, doxycycline, oxytetracycline, demeclocycline, lymecycline, meclocycline, methacycline, rolitetracycline, chlorotetracycline or tigecycline. In certain embodiments the tetracycline is a mixture of two or more tetracyclines. In one or more preferred embodiments the tetracycline is minocycline or its pharmaceutically acceptable salt. In one or more preferred embodiments the tetracycline is minocycline hydrochloride. The active ingredient or its pharmaceutically acceptable salt is present in the topical composition in therapeutically effective amounts. The concentration of active ingredient will vary with the particular dosage form and the disease state for which it is intended.

The nanoparticulate topical composition according to the present invention comprises one or more non-aqueous liquid vehicle. The non-aqueous liquid vehicle excludes aqueous vehicles or protic solvents that contain water, such as for example water, glycols, alcohols, acids or bases. The suitable examples of the non-aqueous vehicle include, but are not limited to, silicon fluids, non-volatile oils or mixtures thereof. It may further include emollients, gelling agents, viscosity builders, or other non-aqueous pharmaceutically acceptable excipients that are suitable for topical application. Suitably, the concentration of non-aqueous liquid vehicle used in the nanoparticulate topical composition and the non-aqueous nanosuspension according to the present invention may range from about 1% to about 99%, from 2.0% w/w to about 95.0% w/w, from about 10.0% w/w to about 95.0% w/w.

In one preferred embodiment, the non-aqueous liquid vehicle comprises a silicon fluid. In another preferred embodiment, the non-aqueous liquid vehicle comprises a mixture of silicon fluid and a non-volatile oil. Suitably, the silicon fluid may be selected from silicones, silicone derivatives or siloxanes. Non limiting example of silicon fluids includes linear or cyclic alkyl siloxanes, aryl siloxanes, alkylether siloxanes, haloalkyl siloxanes, polycycloxanes, siloxane polymers, other functionalized siloxanes and the like and mixtures thereof. In preferred embodiment, the silicon fluid is selected from cyclopoly dimethyl siloxane (cyclomethicone example decamethylcyclopentasiloxane); poly dimethyl siloxane (silicon oils such as dimethicone) or mixture thereof. Other representative silicon fluids that may be used include, hexamethyldisiloxane, decamethyltetrasiloxane, dodecamethylpentasiloxane, tetradecamethylhexasiloxane, hexadecamethylheptasiloxane, hexamethylcyclotrisiloxane, octamethylcyclotetrasiloxane, dodecamethylcyclohexasiloxane. Suitably, the non-volatile oil is selected from mineral oil, paraffin oil, castor oil, olive oil, sesame oil, soybean oil, peanut oil, coconut oil, avocado oil, jojoba oil, grape seed oil, jojaba oil, corn oil, cottonseed oil, white petrolatum, white soft paraffin, shea butter, triglycerides like labrafac, triacetin, capric/caprylic triglyeride, octyl dodecanol, diisopropyl adipate, light mineral oil and the like and mixtures thereof. In preferred embodiment, the non-aqueous liquid vehicle comprises cyclomethicone or a mixture of cyclomethicone and mineral oil.

Suitably, the one or more wetting agents according to the present invention comprise one or more wetting agent having a HLB value from 1 to 10. Preferably the wetting agent is a non-ionic surfactant. More preferably the wetting agent is a non-ionic surfactant having a HLB value from 1 to 10. More preferably, the wetting agent is a non-ionic surfactant which is chemically similar to the non-aqueous liquid vehicle, for example wetting agent is a silicon based surfactant when the non-aqueous liquid vehicle is a silicone fluid. The non-ionic surfactants as the wetting agent that can be used in the context of the present invention includes, but are not limited to silicon based non-ionic surfactants; Sorbitan esters (such as Span®80); Sucrose stearic acid esters; glyceryl monostearate, glyceryl monooleate, macrogolglycerol; hydroxy stearates (PEG 7 hydrogenated castor oil), PEGS castor oil and the like and mixtures thereof. Non-limiting examples of silicon based non-ionic surfactants that can be used in the context of the present invention includes dimethicone copolyol polymer or cyclomethicone-dimethicone copolyol polymer [(available in market under the brand name DC5225C®, by Dow Corning company and is chemically poly(oxyethylene. oxypropylene) methyl polysiloxane copolymer, INCI name is cyclopentasiloxane-PEG/PPG-18/18 Dimethicone)], silicone phosphate ester polymer, a silicone sulfate polymer, a silicone carboxylate polymer, a silicone sulfosuccinate polymer, a silicone sulfonate polymer, a silicone thiosulfate polymer, a silicone amphoteric polymer, a silicone betaine polymer, a silicone phosphobetaine polymer, a silicone alkyl quaternary polymer, a silicone quaternary polymer, a silicone imidazoline quaternary polymer, a silicone carboxy quaternary polymer, a silicone alkanolamide polymer, a silicone ester polymer and mixtures thereof. In preferred embodiments, the nanoparticulate topical composition or the non-aqueous nanosuspension comprises the silicon based non-ionic surfactants like cyclomethicone-dimethicone copolyol polymer. Suitably, in preferred embodiments, the nanoparticulate topical composition or non-aqueous nanosuspension is free of ionic surfactants.

Suitably, the concentration of wetting agents used in the nanoparticulate topical composition according to the present invention may range from about 0.5% by weight to about 20.0% by weight, such as about 1.0, 1.5, 2.0, 2.5, 3.0, 3.5, 4.0, 4.5, 5.0, 6, 7, 8, 9, 10, 11, 12, 13, 14, 15, 16, 17, 18, or 19% by weight, preferably from about 1.0% by weight to about 10.0% by weight of the composition, more preferably from about 1.0% by weight to about 5.0% by weight of the composition.

Suitably, the concentration of wetting agents used in the non-aqueous nanosuspension according to one embodiment of the present invention may range from about 1.0% by weight to about 50.0% by weight, more preferably from about 2.0% by weight to about 40.0% by weight, more preferably from about 3.0% by weight to about 30.0% by weight of the nanosuspension. In preferred embodiments, the ratio of the water soluble active ingredient or its salt to the wetting agent in the non-aqueous nanosuspension can vary from about 1:0.1 to about 1:10.

In some embodiments, the nanoparticulate topical compositions may further include excipients such as, but not limited to, a penetration enhancer like isopropyl myristate, isopropyl palmitate, oleic acid etc.; an antioxidant such as butylated hydroxy anisole, butylated hydroxy toluene, tocopherol succinate, propyl gallate, tocopherol, (vitamin E), tocopherol sorbate, tocopherol acetate, other esters of tocopherol, butylated hydroxy benzoic acids and the like; a preservative such as $C_{12}$ to $C_{15}$ alkyl benzoates, alkyl p-hydxoxybenzoates, ascorbic acid, benzalkonium chloride, sorbic acid, citric acid, benzoic acid, benzoic acid esters of $C_9$ to $C_{15}$ alcohols, chlorocresol, methyl paraben, propyl paraben, sodium benzoate and the like; a surfactant such as a non-ionic surfactant. Other suitable ingredients known in the art, for instance, a tonicity modifier, a viscosity modifier, an anti perspirant, an anti-static agent, a chelating agent, a colorant, a diluent, a humectant, an occlusive agent, a perfuming agent, a sunscreen, or other suitable agents may optionally be incorporated in the topical pharmaceutical compositions of the present invention. Any suitable agent in each group that is non-aqueous and suitable for topical pharmaceutical application may be used. The excipients may be used in suitable amounts known, which can be readily determined by one of ordinary skill in the art, so as to get compositions having desired properties.

In one preferred embodiment, the nanoparticulate topical compositions include penetration enhancer like isopropyl myristate, isopropyl palmitate, oleic acid and the like. Suitably, the penetration enhancer may be used in an amount ranging from about 1% to about 30% by weight, preferably from about 5% to 25% by weight, more preferably from about 10% to about 20% by weight.

Suitably, the at least one rheology modifier that can be used in the foam or aerosol or ointment or lotion type nanoparticulate topical composition according to the present invention, includes, but are not limited to, silicone based thickening agent such as 'Elastomer 10®' (crosspolymer of cyclopentasiloxane and dimethicone); ST wax 30®; Gelucire®43/01 (glycerol esters of saturated $C_{12}$-$C_{18}$ fatty acids); petrolatum, or other suitable agents and mixtures thereof.

The nanoparticulate topical composition of the present invention is a topical dosage form such as foam, gel, ointment, suspension, aerosol, spray, cream or lotion or the like.

The nanoparticulate topical composition according to one preferred embodiment the present invention is a non-aqueous nanosuspension which may be applied as such or may take the form of a suitable formulation such as spray formulation.

In preferred embodiments, wherein the nanoparticulate topical composition is a gel, the non-aqueous liquid vehicle comprises a silicon fluid and/or mineral oil, at least one gelling agent and at least one emollient. A penetration enhancer, an antioxidant, a preservative, a viscosity builder such as cetostearyl alcohol and/or a surfactant or other suitable agents may optionally be used.

In one particular embodiment, the non-aqueous nanoparticulate topical composition is a gel and it comprises a water soluble and water susceptible active ingredient, a wetting agent and a non-aqueous liquid vehicle comprising a silicon fluid, at least one gelling agent, at least one emollient, a viscosity builder such as cetostearyl alcohol, a penetration enhancer and an antioxidant. In another particular embodiment, the non-aqueous nanoparticulate topical composition is a gel and it comprises a water soluble and water susceptible active ingredient, a wetting agent and a non-aqueous liquid vehicle comprising a silicon fluid, a mineral oil, at least one gelling agent, at least one emollient, a viscosity builder such as cetostearyl alcohol, a penetration enhancer and an antioxidant.

Suitably, the at least one gelling agent that can be used in the gel composition according to the present invention includes, but are not limited to, silicone based gelling/thickening agent such as 'Elastomer 10®' which is chemically a crosspolymer of cyclopentasiloxane and dimethicone; ST wax 30®, which is chemically an alkylmethyl silicone wax and the like and mixtures thereof. ST wax 30® also acts as an emollient.

Suitably, the at least one emollient that can be used in the topical gel composition according to the present invention includes, but are not limited to, silicone based emollients such as ST wax 30® which is chemically an alkylmethyl silicone wax, Silky wax 30® which is chemically stearoxytrimethylsilane and stearyl alcohol, cyclomethicone, dimethicone, dimethiconol (hydroxy terminated polydimethylsiloxane), disiloxane and the like; other waxes like white ceresin wax (mixture of paraffin and microcrystalline waxes), oily emollients such as mineral oil or other suitable emollients.

In another preferred embodiment, wherein the nanoparticulate topical composition is a foam or an aerosol, the non-aqueous liquid vehicle comprises a silicon fluid and/or mineral oil, at least one foaming agent, at least one surfactant, at least one non-aqueous liquid (that can act as a foam breaking agent), at least one rheology modifier and at least one propellant. A penetration enhancer, an antioxidant, a preservative or other suitable agents used in foam compositions may optionally be used.

In one particular embodiment, the non-aqueous nanoparticulate topical composition is a foam and it comprises a water soluble and water susceptible active ingredient, a wetting agent and a non-aqueous liquid vehicle comprising a silicon fluid, a mineral oil, at least one foaming agent, at least one surfactant, at least one rheology modifier, at least one non-aqueous liquid which impart foam breakability and at least one propellant.

Suitably, the at least one foaming agent (also known as foam adjuvants) that can be used in the nanoparticulate topical foam composition according to the present invention includes, but are not limited to, oleyl alcohol, stearyl alcohol, myristyl alcohol, cocoglyerides, behenyl alcohol, palmitic acid, stearic acid, oleic acid and the like and mixtures thereof.

Suitably, the at least one propellant that can be used in the foam or aerosol nanoparticulate topical composition according to the present invention, includes, but are not limited to, compressed gases, volatile hydrocarbons such as butane, propane, isobutane, halo hydrocarbon propellants, and the like or mixtures thereof. Preferably, the propellants are hydrocarbon propellants such as NIP-70 (combination of Propane/Isobutane/n-butane in a ratio of 55/15/30 and having a vapor pressure of 70 psig); HARP-AP40 (combination of Propane/Isobutane/n-butane, in a ratio of 22/24/54 and having a vapor pressure of 40 psig) and the like.

Suitably, the at least one non-aqueous liquid that can be used in the foam nanoparticulate topical composition according to the present invention includes silicon fluids and/or oils such as but not limited to disiloxane, cyclomethicone, dimethicone, dimethiconol (hydroxy terminated polydimethylsiloxane), mineral oil and the like and mixtures thereof. These liquids can act as a foam breaking agent or spreading agent.

In another preferred embodiment, wherein the nanoparticulate topical composition is an ointment or a lotion, the non-aqueous liquid vehicle comprises a silicon fluid and/or mineral oil, at least one non-aqueous liquid (which acts as a spreading agent), at least one rheology modifier, at least one surfactant, at least one ointment base like petrolatum. A penetration enhancer, an antioxidant, a preservative or other suitable agents used in formulating ointment/lotion compositions, may optionally be used.

The at least one surfactant that can be used in the gel, foam, aerosol, ointment, lotion composition according to the present invention, preferably includes a non-ionic surfactant such as silicon based non-ionic surfactants such as dimethicone copolyol polymer or cyclomethicone-dimethicone copolyol polymer; sorbitan esters such as Span®80; sucrose stearic acid esters; glyceryl monostearate, glyceryl monooleate, macrogolglycerol; hydroxy stearates (PEG 7 hydrogenated castor oil), PEG5 castor oil and the like and mixtures thereof.

According to one particularly preferred embodiment, the nanoparticulate topical compositions of the present invention include minocycline or its pharmaceutically acceptable salts as the water soluble and water susceptible active ingredient. Preferably, minocycline or its pharmaceutically acceptable salts is Minocycline hydrochloride, which has the following structure:

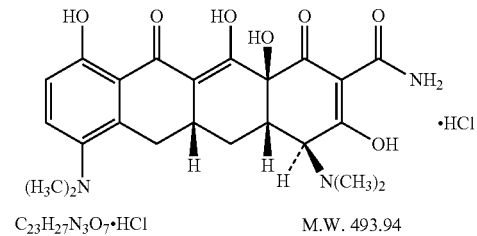

$C_{23}H_{27}N_3O_7 \cdot HCl$    M.W. 493.94

Minocycline or its pharmaceutically acceptable salt is present in the compositions in therapeutically effective amounts. Preferably, the effective amount of Minocycline or its pharmaceutically acceptable salt present in the nanoparticulate topical composition is such that it is sufficient to treat or prevent acne, rosacea or related disorders of the skin when applied topically. The dosages of minocycline salts will be understood to be on the basis of the amount of minocycline free base provided thereby, and thus may be expressed as a minocycline free base equivalent dosage or amount. Minocycline or its pharmaceutically acceptable salt is present in the non-aqueous nanosuspension at a concentration ranging from about 0.01% to about 15% by weight, such as about 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.74, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, 7.0, 7.5, 8.0, 8.5, 9.0, 9.5, 10, 11, 12, 13, 14 or 15% by weight, preferably about 0.1% to about 10% by weight, more preferably about 0.5% to about 5% by weight of the nanosuspension. The nanoparticulate topical composition typically contain an effective amount, e.g., about 0.01% to about 10% by weight (w/w), such as about 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.74, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, 7.0, 7.5, 8.0, 8.5, 9.0, 9.5 or 10% by weight, preferably about 0.01% to about 5% by weight, more preferably about 0.1% to about 3% by weight, more preferably about 0.2% to about 1.5% by weight of minocycline or its salt. The concentration of active ingredient will vary with the particular dosage form and the disease state for which it is intended. In most preferred embodiments, the minocycline or its salt is present in the nanoparticulate topical pharmaceutical composition at a concentration of about 0.5% or 1.0% or 2% by weight. hydrochloride. In one preferred embodiment, minocycline hydrochloride used in the nanoparticulate composition of the present invention is crystalline in nature. In one embodiment, the crystalline nature of the active is maintained even after nano-milling and the non-aqueous nanosuspension and the topical composition of the present invention essentially comprises minocycline in crystalline form.

In one specific embodiment, the present invention provides a nanoparticulate minocycline topical composition, comprising nanoparticles of minocycline or its pharmaceutically acceptable salt, one or more wetting agents and a non-aqueous liquid vehicle.

In one specific embodiment, the present invention provides a nanoparticulate minocycline topical composition in the form of a gel, comprising nanoparticles of minocycline or its pharmaceutically acceptable salts, one or more wetting agents, and a non-aqueous liquid vehicle comprising pharmaceutically acceptable, non-aqueous topical gel excipients. In another specific embodiment, the present invention provides a nanoparticulate minocycline topical composition in the form of foam, comprising nanoparticulate minocycline or its pharmaceutically acceptable salts, one or more wetting agents and a non-aqueous liquid vehicle comprising pharmaceutically acceptable, non-aqueous topical foam excipients.

In a preferred embodiment, the present invention provides a nanoparticulate minocycline topical composition comprising nanoparticles of minocycline or its pharmaceutically acceptable salt having a particle size distribution such that 90% of the particles are less than 1000 nm in size, one or more wetting agents and a non-aqueous liquid vehicle, wherein the composition is free of water.

In one or more embodiment, the present invention provides a nanoparticulate minocycline topical composition comprising nanoparticles of minocycline or its pharmaceutically acceptable salt having a particle size distribution such that 90% of the particles ($D_{90}$) are less than 1000 nm and 50% of the particles ($D_{50}$) are less than 800 nm, one or more wetting agents and a non-aqueous liquid vehicle, wherein the composition is free of water. In a preferred embodiment, the present invention provides a nanoparticulate minocycline topical composition comprising nanoparticles of minocycline or its pharmaceutically acceptable salt having a particle size distribution such that 90% of the particles are less than 1000 nm in size, one or more wetting agents and a non-aqueous liquid vehicle, wherein the composition is prepared by a method comprising steps of mixing minocycline or its pharmaceutically acceptable salts, one or more wetting agents and a non-aqueous liquid vehicle; incorporating inert grinding media to the above mixture; milling the mixture; and separating the inert grinding media to obtain a nanoparticulate nanosuspension, and optionally converting the nanosuspension into nanoparticulate topical compositions (such as a gel or foam or aerosol or spray or ointment or lotion or cream) by mixing the nanosuspension with pharmaceutically acceptable topical vehicle excipients.

According to preferred embodiments of the invention, the particle size distribution of minocycline or its pharmaceutically acceptable salt present in the nanoparticulate minocycline topical composition is such that $D_{90}$ is less than 1000 nms and $D_{50}$ is less than 800 nms. According to preferred embodiments of the invention, the one or more wetting agent is cyclomethicone-dimethicone copolyol polymer (a silicon based non-ionic surfactants) and the non-aqueous liquid vehicle comprises cyclomethicone, mineral oil or mixture thereof. It may further comprise other pharmaceutically acceptable topical non-aqueous liquid vehicle excipients.

In a particularly preferred embodiment, the present invention provides a nanoparticulate minocycline topical composition comprising minocycline or its pharmaceutically acceptable salt having a particle size distribution such that 90% of the particles ($D_{90}$) are less than 1000 nm and 50% of the particles ($D_{50}$) are less than 800 nm in size, one or more wetting agents, a non-aqueous liquid vehicle, wherein the wetting agent is cyclomethicone-dimethicone copolyol polymer (a silicon based non-ionic surfactants), and the non-aqueous liquid vehicle comprise cyclomethicone or a mixture of cyclomethicone and mineral oil. In one particularly preferred embodiment, it further comprises a penetration enhancer.

According to some preferred embodiments, the present invention provides nanoparticulate topical composition of minocycline hydrochloride in the form of a gel comprising—

| Ingredients | Amount % w/w |
|---|---|
| Minocycline or its pharmaceutically acceptable salt | 0.01% to 10.0% |
| Wetting agent | 0.5% to 20.0% |
| Non-aqueous silicon fluid | 5.0% to 95.0% |
| Oil | 0.0% to 30.0% |
| Emollient | 1.0% to 10.0% |
| Antioxidant | 0.0% to 1.0% |
| Gelling agent | q.s. to 100% |

According to specific preferred embodiments, the present invention provides nanoparticulate topical composition of minocycline hydrochloride in the form of a gel comprising—

| Ingredients | Amount % w/w |
|---|---|
| Minocycline hydrochloride | 0.01% to 10.0% |
| Cyclomethicone Dimethicone Copolyol | 0.5% to 20.0% |
| Cyclomethicone | 5.0% to 95.0% |
| Mineral Oil | 0.0% to 30.0% |
| Alkylmethyl silicone wax (ST Wax 30) | 1.0% to 10.0% |
| Cetostearyl Alcohol | 0.0% to 10.0% |
| Butylated Hydroxy Anisole | 0.0% to 1.0% |
| Cyclopentasiloxane and dimethicone crosspolymer (Elastomer 10) | q.s. to 100% |

According to specific preferred embodiments, the present invention provides nanoparticulate topical composition of minocycline hydrochloride in the form of a gel comprising:

| Ingredients | % w/w |
| --- | --- |
| Minocycline hydrochloride | 1.0 |
| Cyclomethicone | 25.0 |
| Cyclomethicone Dimethicone Copolyol | 2.3 |
| Alkylmethyl silicone wax (ST Wax 30) | 4.0 |
| Cetostearyl Alcohol | 8.0 |
| Butylated Hydroxy Anisole | 0.1 |
| Cyclopentasiloxane and dimethicone crosspolymer (Elastomer 10) | q.s. to 100 |

According to specific preferred embodiments, the present invention provides nanoparticulate topical composition of minocycline hydrochloride in the form of a gel comprising:

| Ingredients | % w/w |
| --- | --- |
| Minocycline hydrochloride | 1.0 |
| Cyclomethicone | 13.0 |
| Cyclomethicone Dimethicone Copolyol | 2.3 |
| Mineral Oil | 12.0 |
| Alkylmethyl silicone wax (ST Wax 30) | 4.0 |
| Cetostearyl Alcohol | 8.0 |
| Butylated Hydroxy Anisole | 0.1 |
| Cyclopentasiloxane and dimethicone crosspolymer (Elastomer 10) | q.s. to 100 |

According to some preferred embodiments, the present invention provides nanoparticulate topical composition of minocycline hydrochloride in the form of a foam comprising—

| Ingredients | Amount % w/w |
| --- | --- |
| Minocycline or its pharmaceutically acceptable salt | 0.01% to 10.0% |
| Wetting Agent | 0.5% to 20.0% |
| Non-aqueous silicon fluid | 5.0% to 95.0% |
| Oil | 2.0% to 30.0% |
| Foaming agent/Foam adjuvant | 1.0% to 10.0% |
| Non-ionic surfactant | 1.0% to 10.0% |
| Rheology modifier | 1.0% to 40.0% |
| Non-aqueous liquid _for imparting foam breakability | 5.0% to 50.0% |
| Propellant | 4-20% of foam composition |

According to some preferred embodiments, the present invention provides nanoparticulate topical composition of minocycline hydrochloride in the form of a foam comprising—

| Ingredients | Amount- % w/w |
| --- | --- |
| Minocycline hydrochloride | 0.01% to 10.0% |
| Cyclomethicone Dimethicone Copolyol | 0.5% to 20.0% |
| Cyclomethicone/Mineral Oil | 10.0% to 95.0% |
| Stearyl alcohol and/or Cetyl alcohol | 1.0% to 10.0% |
| Glyceryl monosteaate | 1.0% to 10.0% |
| Glycerol ester of higher saturated fatty acid (Gelucire 43/01) | 1.0% to 10.0% |
| Mineral oil | 2.0% to 30.0% |
| Disiloxane (hexadimethyl disiloxane and octamethyltrisiloxane) | 5.0% to 50.0% |
| Cyclopentasiloxane and dimethicone crosspolymer (Elastomer 10) | 5.0% to 40.0% |
| Hydrocarbon propellant - propane/isobutane/n-butane, 55/15/30 (NIP-70) | 4-20% of foam composition |

The nanoparticulate topical compositions according to the present invention such as the non-aqueous nanosuspensions, the gel and foam compositions were found to be physically and chemically stable upon manufacture and storage. The non-aqueous nanosuspension of the present invention show proper suspension behavior and is physically stable for at least three months. No significant change in particle size distribution of minocycline or its salt was observed upon storage. Further, the nanosuspension as well as nanoparticulate topical compositions did not showed any sign of chemical degradation. The chemical assay of minocycline did not substantially change upon storage and remains within the specified limit of 90-110% of label claim. The impurity profile or contents of related substances or total impurities remains within the specified limits, of not more than 4% upon storage.

The nanoparticulate topical compositions of the present invention are useful in the treatment of acne, rosacea, impetigo or a skin disease caused by bacteria (such as *Staphylococcus aureus, Streptococcus pyogenes, Escherichia coli, Pseudomonas aeruginosa*, a methicillin resistant *Staphylococcus aureus* bacteria), by topical application of the nanoparticulate topical compositions to the affected diseased area of the skin, mucosa or eye. The present invention provides a method of treating acne, rosacea, impetigo or a skin disease caused by bacteria, by topical application of a non-aqueous nanoparticulate topical composition comprising nanoparticles of a water soluble active ingredient or its pharmaceutically acceptable salt, having a particle size distribution such that 90% of the particles are less than 1000 nm. The present inventors have discovered that compositions containing nanoparticles of minocycline or its pharmaceutically acceptable salts, according to the present invention provides improved efficacy in treating acne.

In one embodiment there is provided a composition according to the present disclosure for use as a medicament.

In one embodiment there is provided a composition according to the present disclosure for use in the treatment of acne, rosacea, impetigo or a skin disease caused by bacteria.

In one particular embodiment there is provided a composition for use in the treatment of acne, rosacea, impetigo or a skin disease caused by bacteria, wherein the composition comprises i. nanoparticles of a water soluble, water-susceptible active ingredient or its pharmaceutically acceptable salt, having a particle size distribution such that 90% of the particles are less than 1000 nm.

ii. one or more wetting agent and iii. a non-aqueous liquid vehicle further wherein the composition is free of water.

According to one embodiment of the present invention, the nanoparticulate topical composition is prepared by a method comprising steps of— i. mixing the water soluble, water-susceptible active ingredient or its pharmaceutically acceptable salt, one or more wetting agents, a non-aqueous liquid vehicle ii. incorporating at least one inert grinding medium in mixture of step (i)

iii. milling the mixture of step (ii)
iv. separating the at least one inert grinding medium from the milled mixture of step (iii) to obtain a non-aqueous nanosuspension and
v. converting the non-aqueous nanosuspension of step (iv) into a topical composition.

The nanoparticulate topical compositions and/or non-aqueous nanosuspension herein above mentioned may be prepared by method/s described below in detail with possible alternative steps and process parameters. The water soluble active ingredient or its salt and the wetting agent, can be dispersed or mixed in a non-aqueous liquid vehicle using suitable agitation means such as, for example, stirring, using a roller mill or a cowles type mixer, until a homogeneous dispersion is achieved. Alternatively, the water soluble active ingredient can be dispersed in a premix of non-aqueous liquid vehicle and the wetting agent. This is followed by incorporation of inert grinding media in mixture and milling the mixture in the presence of grinding media, so as to reduce the particle size and obtain nanoparticles of water soluble active ingredient or its pharmaceutically acceptable salt. The mechanical means used to reduce the effective mean particle size of water soluble active ingredient or its pharmaceutically acceptable salt, conveniently can take the form of dispersion or grinding mill. Suitable dispersion mills include a ball mill, an attrition mill, a vibratory mill, a planetary mill, media mills—such as a sand mill and a bead mill. In preferred embodiments, a media mill is used due to the relatively shorter milling time required to provide the desired reduction in particle size.

The grinding media for the particle size reduction step can be selected from rigid media preferably spherical beads having a mean size less than 3 mm, preferably less than 1 mm, preferably in the range of about 0.07 mm to 1.0 mm, more preferably in the range of about 0.2 mm to 0.4 mm. In one embodiment, a combination of small and large size grinding media may be used. Such media desirably can provide the particles of the invention with shorter processing times and impart less wear to the milling equipment. The selection of the material for the grinding media is believed not to be critical. However, 95% ZrO stabilized with yttrium, magnesia, zirconium silicate, glass, titanium or alumina provide particles having levels of contamination which are believed to be acceptable for the preparation of pharmaceutical compositions. Further, other media, such as glass, stainless steel, titanium, alumina, polymeric beads/resins like crosslinked polystyrene & methyl methacrylate or beads made up of biodegradable polymers, may be used. Preferably, in one embodiment, the grinding media is 95% ZrO stabilized with yttrium.

The preferred proportions of the grinding media, the water soluble active agent, the non-aqueous liquid vehicle, and wetting agent present in the grinding vessel can vary within wide limits and depends, for example, upon the size and density of the grinding media, the type of mill selected, etc. The attrition time may vary and depends primarily upon the mechanical means and residence conditions selected, the initial and final particle size and so forth. In one or more embodiments, the milling is carried out for a period of about 30 minutes to about 48 hours. The method can be carried out within a wide range of temperatures and pressures. In preferred embodiments, milling is carried out at a processing temperature of less than 40° C. In preferred embodiments, the processing temperatures of around 20° C. to 40° C. for grinding are ordinarily preferred. If desired, the processing equipment may be cooled with conventional cooling equipment. The method is conveniently carried out under conditions of ambient temperature and at processing pressures which are safe and effective for the milling process and at which the active agent is stable. The grinding media is separated from the milled particulate agent using conventional separation techniques, in a secondary process such as by simple filtration, sieving through a mesh filter or screen, and the like. Other separation techniques such as centrifugation may also be employed to obtain the non-aqueous nanosuspension. In one specific embodiment, milling may be performed by using a bead mill (model—NETZSCH Feinmahltechnik GmbH) comprising beads made up 95% ZrO stabilized with yttrium, having a bead size ranging from about 0.2 mm to 0.4 mm, the milling being carried out at a processing temperature of less than 40° C. and for a period of about 30 minutes or more. According to this embodiment, the nanoparticles of water soluble active ingredient or its pharmaceutically acceptable salts have a particle size distribution such that 90% of the particles ($D_{90}$) are less than 1000 nm and 50% of the particles ($D_{50}$) are less than 800 nm. The non-aqueous nanosuspension so obtained is converted into a topical composition. This is achieved by mixing the non-aqueous nanosuspension with pharmaceutically acceptable topical vehicle excipients or vice-versa to obtain the nanoparticulate topical composition. This can be achieved either by first mixing the excipients of the non-aqueous topical vehicle under appropriate temperature and/or stirring condition to get a excipient mixture with uniform consistency followed by addition of the non-aqueous nanosuspension of the water soluble active ingredient; or alternatively it can be achieved by addition of various topical excipients to the non-aqueous nanosuspension and then mixing under appropriate temperature and/or stirring condition to obtain the topical composition. The sequence and steps of addition of non-aqueous topical vehicle excipients may vary depending upon the dosage form and excipients used.

In the context of this specification "comprising" is to be interpreted as "including".

Aspects of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

Hereinafter, the invention will be more specifically described by way of Examples. The examples are not intended to limit the scope of the invention and are merely used as illustrations.

EXAMPLES

Examples 1-5 gives the composition and process of preparing the topical non-aqueous nanosuspension composition of minocycline hydrochloride.

TABLE 1

Details of the Non-aqueous nanosuspension composition

| Category of Ingredients | Ingredient | Quantity (in grams) | | | | |
|---|---|---|---|---|---|---|
| | | Example 1 | Example 2 | Example 3 | Example 4 | Example 5 |
| Active agent | Minocycline Hydrochloride | 5.6 | 3.07 | 3.00 | 3.07 | 7.31 |
| Non-aqueous Liquid vehicle | Cyclomethicone | 140.0 | 76.86 | 39.0 | 76.86 | 91.4 |
| Non-aqueous Liquid vehicle | Mineral Oil | — | — | 36.0 | 36.0 | — |
| Wetting agent | Cyclomethicone Dimethicone Copolyol | 6.0 | 7.07 | 9.00 | 6.9 | 14.62 |

Method of preparation of non-aqueous nanosuspension: Minocycline was dispersed in cyclomethicone along with cyclomethicone dimethicone copolyol and mixed. To this was added, inert grinding media made up of 95% ZrO stabilized with magnesia and having diameter of 0.4 mm. The mixture was stirred for about 24 hours and milling carried out. The inert grinding media was separated and the resulting nanosuspension was analysed for recording the 'particle size distribution' of minocycline nanoparticles using Malvern Mastersizer (MS3000).

The results of Malvern particle size analysis for nanosuspensions of example 1-5 is presented below in Table 2.

TABLE 2

Particle Size Distribution (PSD) Results for nanosuspension of Example 1-5:

| PSD (nm) | Example 1 | Example 2 | Example 3 | Example 4 | Example 5 |
|---|---|---|---|---|---|
| $D_{10}$ | 235 | 177 | 250 | 146 | 187 |
| $D_{50}$ | 368 | 256 | 393 | 232 | 274 |
| $D_{90}$ | 589 | 369 | 613 | 339 | 403 |

In various examples, the mean particle size of the minocycline hydrochloride is such that 50% of the particles ($D_{50}$) have a diameter varying from 200 nms to about 400 nms, and 90% of the particles ($D_{90}$) have a diameter of less than 1000 nms.

The non-aqueous nanosuspension of Example 1 & 5 were subjected to storage stability study by keeping the nanosuspension in an amber colored glass vial at room temperature (25° C./60% relative humidity) for at least 3 months. The physical appearance, change in particle size distribution, and chemical assay of Minocycline hydrochloride were evaluated after 3 months. The analysis of assay of minocycline hydrochloride, related substances and total impurities was done using HPLC technique. The observations are given in Table 3 & 4 below:

TABLE 3

Stability study results of nano-suspension of Example 1:

| Time point | Particle Size Distribution (nm) | | | Chemical Assay | Physical Appearance |
|---|---|---|---|---|---|
| | $D_{10}$ | $D_{50}$ | $D_{90}$ | | |
| Initial | 235 | 368 | 589 | 99.43% | Suspension |
| 3 Month | 210 | 311 | 463 | 104.73% | Suspension |

TABLE 4

Stability study results of nano-suspension of Example 5:

| Time point | Particle Size Distribution (nm) | | | Chemical Assay | 4-Epi Mino-cycline | Physical Appearance |
|---|---|---|---|---|---|---|
| | $D_{10}$ | $D_{50}$ | $D_{90}$ | | | |
| Initial | 187 | 274 | 403 | 107.24 | 0.89 | Suspension |
| 3 Month | 188 | 273 | 400 | 105.65 | 0.91 | Suspension |

The non-aqueous nanosuspension of the present invention was found to be physically and chemically stable upon manufacture and storage for at least 3 months. No significant change in particle size distribution of minocycline or its salt was observed upon storage. Further, the nanosuspension did not showed any sign of chemical degradation as the chemical assay of minocycline did not changed upon storage. The contents of related substances and total impurities remained within the specified limits, upon storage.

Examples 6-10

The non-aqueous nanosupensions (prepared as per method described in Example 1-5) were converted into topical compositions in the form of a gel whose details are given below in Table 5:

TABLE 5

Details of the nanoparticulate topical composition in the form of gel:

| Description | Ingredients | Function of Ingredients | Amount-% w/w | | | | |
|---|---|---|---|---|---|---|---|
| | | | Example 6 | Example 7 | Example 8 | Example 9 | Example 10 |
| ** Non-aqueous nanosuspension | Minocycline hydrochloride | Active agent | 1.0 | 1.0 | 1.0 | 1.0 | 1.0 |
| | Cyclomethicone | Non aqueous Vehicle | 25.0 | 13.0 | 25.0 | 25.0 | 25.0 |

TABLE 5-continued

Details of the nanoparticulate topical composition in the form of gel:

| Description | Ingredients | Function of Ingredients | Amount-% w/w | | | | |
|---|---|---|---|---|---|---|---|
| | | | Example 6 | Example 7 | Example 8 | Example 9 | Example 10 |
| | Cyclomethicone Dimethicone Copolyol | Wetting agent | 2.3 | 2.3 | 2.3 | 2.3 | 2.3 |
| | Mineral Oil | Non aqueous Vehicle | — | 12.0 | — | — | — |
| Topical gel non-aqueous liquid vehicle | Alkylmethyl silicone wax (ST Wax 30) | Emollient and thickener | 4.0 | 4.0 | 4.0 | 4.0 | — |
| | White Ceresin Wax | Emollient and thickener | — | — | — | — | 4.0 |
| | Oleic acid | Penetration enhancer | — | — | 10.0 | — | — |
| | Isopropyl myristate | Penetration enhancer | — | — | — | 20.0 | 20 |
| | Cetostearyl Alcohol | Viscosity builder | 8.0 | 8.0 | 8.0 | 8.0 | 8.0 |
| | Butylated Hydroxy Anisole | Antioxidant | 0.1 | 0.1 | 0.1 | 0.1 | 0.1 |
| | Cyclopentasiloxane and dimethicone cross-polymer (Elastomer 10) | Gelling agent | q.s. to 100 | q.s. to 100 | q.s to 100 | q.s to 100 | q.s to 100 |

** The non aqueous nanosuspensions used in formulating the gel compositions comprised of nanoparticles of minocycline having a particle size distribution such that 90% of the particles ($D_{90}$) have a size in the range of 200 to 700 nms, 50% of the particles ($D_{50}$) have a size in the range of 100 to 500 nms, and 10% of the particles ($D_{10}$) have a size in the range of 50 to 300 nms.

Method of preparation of nanoparticulate minocycline topical gel composition: ST wax 30 and cetostearyl alcohol were melted at a temperature of 70-75° C. and butylated hydroxy anisole (and oleic acid as in example 8 or isopropyl myristate as in example 9 & 10) was added to this mixture. The melted mixture was added to Elastomer10 under stirring. To this was added minocycline hydrochloride nanosuspension (containing minocycline hydrochloride, cyclomethicone and/or mineral oil, and cyclomethicone dimethicone copolyol, prepared as per method of example 1-5) and the mixture was stirred at 35° C. to attain uniform consistency. This resulted in the formation of a non-greasy, anhydrous topical gel composition.

The non-aqueous nanoparticulate compositions so prepared were subjected to storage stability testing by storing the composition at room temperature (25° C./60% relative humidity) in white collapsible tube for at least 3 months. The physical appearance, change in particle size distribution, and chemical assay of minocycline hydrochloride were evaluated after 3 months. It was observed that the compositions were physically and chemically stable upon manufacture and storage for at least 3 months. There occurred no change in physical appearance of the compositions (light yellow coloured semisolid gel) upon storage. The viscosity of the composition also did not change substantially upon storage. Further, the nanosuspension did not showed any sign of chemical degradation as the chemical assay of minocycline was well within the limit of 90%-110% of the label claim upon storage. The related substances and total impurities remained within the specified limits of not more than 4%, upon storage. The observations for composition of Example 10 are given in Table 6 below:

TABLE 6

Stability results of nanoparticulate composition:

| Time point | Impurity: 4-Epi-minocycline | Assay of Minocycline | Physical Appearance | Viscosity (cps) |
|---|---|---|---|---|
| Initial | 0.923 | 105.32 | Light yellow semi-solid gel | 250333 |
| 3 Month | 0.967 | 107.04 | Light yellow semi-solid gel | 251944 |

Note:
The analysis of assay of minocycline hydrochloride and 4-epiminocycline was done using HPLC technique. The viscosity of the composition was determined using a Brookfield ® LVDP + Pro II viscometer at a temperature of 30 ± 2° C.

Example 11-12

The non-aqueous nanosuspension (prepared as per the method described in Example 1-5) were converted into topical compositions in the form of foam, whose details are given in Table 7:

TABLE 7

Details of the topical composition in the form of foam:

| Description | Ingredients | Function of Ingredients | Amount- % w/w | |
|---|---|---|---|---|
| | | | Example 11 | Example 12 |
| **Non-aqueous nanosuspension | Minocycline hydrochloride | Active agent | 1.0 | 1.0 |
| | Cyclomethicone | Non aqueous Vehicle | 25.0 | 13.0 |
| | Cyclomethicone Dimethicone Copolyol | Wetting agent | 2.3 | 2.3 |
| | Mineral Oil | Non aqueous Vehicle | — | 12.0 |

TABLE 7-continued

Details of the topical composition in the form of foam:

| Description | Ingredients | Function of Ingredients | Amount- % w/w Example 11 | Example 12 |
|---|---|---|---|---|
| Topical foam non-aqueous liquid vehicle | Stearyl alcohol | Foam adjuvants | 2.0 | 2.0 |
| | Cetyl alcohol | Foam adjuvants | 1.0 | 1.0 |
| | Glyceryl monosteaate | Non-ionic surfactant | 6.0 | 6.0 |
| | Glycerol ester of higher saturated fatty acid (Gelucire 43/01) | Hard fat | 6.0 | 6.0 |
| | Mineral oil | Oil phase | 20.0 | 12.0 |
| | Disiloxane (hexadimethyl disiloxane and octamethyltrisiloxane) | Impart Foam breakability | 26.7 | 34.7 |
| | Cyclopentasiloxane and dimethicone crosspolymer (Elastomer 10) | Rheology modifier | 10.0 | 10.0 |
| Propellant | Hydrocarbon propellant - propane/isobutane/n-butane, 55/15/30 (NIP-70) | Foam Propellant | 4-20% of foam composition | |

**The non aqueous nanosuspensions used in formulating the gel compositions comprised of nanoparticles of minocycline having a particle size distribution such that 90% of the particles ($D_{90}$) have a size in the range of 200 to 700 nms, 50% of the particles ($D_{50}$) have a size in the range of 100 to 500 nms, and 10% of the particles ($D_{10}$) have a size in the range of 50 to 300 nms.

Preparation of nanoparticulate minocycline topical foam composition: The excipients of foam composition vehicle including Stearyl alcohol, Cetyl alcohol, Glyceryl monosteaate, Gelucire, mineral oil, and Elastomer 10 (except disiloxane) were melted at a temperature of 70° C.-75° C. under stirring to attain a mixture with uniform consistency. The mixture was then cooled to 35° C. and to this, the minocycline hydrochloride nanosuspension (containing minocycline hydrochloride, cyclomethicone and/or mineral oil, and cyclomethicone dimethicone copolyol, prepared as per example 1-4) was added along with disiloxane. The dispersion so obtained had a viscosity of about 3720 cps (as determined by a Brookfield® LVDP+Pro II viscometer at a temperature of 25±2° C.). The dispersion was filled in the foam canister and sealed followed by addition of appropriate amount of propellant. This resulted in the formation of a creamy, quick breaking nanoparticulate topical foam composition.

Example 13

Efficacy Study: The nanoparticulate topical compositions prepared according to the present invention [(1) Nanoparticulate topical gel composition of Example 6 which comprised of particles of minocycline having a particle size distribution such that $D_{90}$ is about 450 nms, $D_{50}$ is about 300 nms and $D_{10}$ is about 200 nms and do not contain any penetration enhancer; and (2) Nanoparticulate topical gel composition of Example 9 which comprised of particles of minocycline having a particle size distribution such that $D_{90}$ is about 310 nms, $D_{50}$ is about 210 nms and $D_{10}$ is about 110 nms and contains isopropyl myristate as a penetration enhancer] were tested for efficacy in treating acne and were compared with prior art known gel or foam compositions that comprise micron size minocycline (comparative example 1 & 2):

The composition details of the comparative examples 1 and 2 are given below:

Comparative Example 1

| Ingredients | Amount (% w/w) |
|---|---|
| Minocycline hydrochloride | 1 |
| Cyclomethicone | 2.96 |
| PPG-15 stearyl ether | 14.82 |
| Octyldodecanol | 11.86 |
| Light mineral oil | 55.03 |
| Glyceryl monostearate | 5.93 |
| Stearyl alcohol | 5.93 |
| Myristyl alcohol | 2.47 |

Comparative Example 2

| Ingredients | Amount- % w/w |
|---|---|
| Minocycline hydrochloride | 1 |
| Versagel M 500 | 69 |
| Mineral oil | 30 |

The comparative examples 1 and 2 comprised of minocycline hydrochloride having a micron size particle size distribution wherein $D_{10}$ was about 1.8 microns, $D_{50}$ is about 10.7 microns and $D_{90}$ is about 29.8 microns.

The nanoparticulate topical compositions prepared according to the present invention (Example 6 and 9) as well as the topical compositions of comparative examples 1 and 2 were tested for efficacy in treating acne. The efficacy of the compositions was determined in *propionibacterium acnes* induced acne in female Sprague Dawley rats. *Propionibacterium acnes* bacteria were injected intradermally into the right ear of rats at day 0, which lead to inflammation and increase in ear thickness. The left ear of all rats was injected with saline (sterile 0.9% sodium chloride solution). The ear thickness of both the ears were measured on day 0, i.e before the injection as well as on day 1. Subsequently starting from day 1, a fixed amount of the compositions of present invention (Example 6 and 9) as well as compositions of comparative examples 1 and 2 was applied topically on the right ear of the animals of the respective groups from day 1 to day 14 daily. The right ear thickness (mm) was periodically measured on day 3, 5, 7, 9, 11, 13, 15 and percentage change in thickness compared to day 1 was calculated. The FIG. 1 illustrates the graph showing right ear thickness at various time points from day 1 to day 14 for various treatment groups i.e. nanoparticulate topical composition of Example 6 (-X-), nanoparticulate topical composition of Example 9 (-▲-); topical composition as per comparative example 1 (-●-) and topical compositions as per comparative examples 2 (-■-).

It was observed that compared to the topical compositions of both comparative examples 1 and 2 which had micron size drug particles, the nanoparticulate topical gel composition of the present invention which comprised of nanoparticles of minocycline but having no penetration enhancer (example 6) showed improved efficacy. Further it was observed that the nanoparticulate topical gel composition of the present invention which comprised of minocycline nanoparticles and have a penetration enhancer such as isopropyl myristate (example 9) showed significantly better efficacy as compared to both the comparative examples 1 and 2. It even showed an improved efficacy as compared to the nanoparticulate topical gel composition of the present invention which did not had a penetration enhancer.

In case of both the nanoparticulate compositions of the present invention, the significant onset of inhibition of *Propionibacterium acnes*-induced inflammation (reduction in ear thickness or acne from day 1), started from day 11, while in case of both the comparative compositions, the significant onset of inhibition or reduction in thickness from day 1, was seen only at day 15. Additionally, the compositions of the present invention showed higher degree of inhibition of *Propionibacterium acnes*-induced inflammation i.e. higher % reduction in ear thickness versus the reduction observed in case of comparative compositions. For instance, the maximum significant ($p<0.001$) inhibition observed in *Propionibacterium acnes*-induced inflammation following topical daily application of nanoparticulate minocycline topical composition of Example 6 and 9 of the present invention were −18.9%, and −23% respectively, on day 15 of the study. While the maximum significant ($p<0.001$) inhibition observed in *Propionibacterium acnes*-induced inflammation following topical daily application of comparative compositions 1 and 2 were −0.9% and −9.7% respectively, on day 15 of the study.

We claim:

1. A nanoparticulate topical composition comprising
   i. nanoparticles of a water soluble, water-susceptible active ingredient or its pharmaceutically acceptable salt, having a particle size distribution such that 90% of the particles are less than 1000 nm
   ii. one or more wetting agent
   iii. at least one gelling agent and
   iv. a non-aqueous liquid vehicle
   wherein the composition is free of water,
   wherein the water soluble, water-susceptible active ingredient is minocycline or its pharmaceutically acceptable salt,
   wherein the one or more wetting agent is cyclopentasiloxane (and) PEG/PPG-18/18 dimethicone, and
   the non-aqueous liquid vehicle comprises cyclomethicone or a mixture of cyclomethicone and mineral oil,
   further wherein the topical composition is a gel.

2. The composition as claimed in claim 1, wherein the nanoparticles have a particle size distribution such that 90% of the particles ($D_{90}$) are less than 1000 nm and 50% of the particles ($D_{50}$) are less than 800 nm.

3. The composition as claimed in claim 1, wherein the nanoparticles have a particle size distribution such that 90% of the particles ($D_{90}$) are less than 700 nm, 50% of the particles ($D_{50}$) are less than 500 nm and 10% of the particles ($D_{10}$) are less than 300 nm.

4. The composition as claimed in claim 1, wherein the water soluble, water susceptible active ingredient is minocycline hydrochloride and it is present in the composition at a concentration ranging from about 0.01% w/w to about 15% w/w.

5. The composition as claimed in claim 1, wherein the wetting agent is present at a concentration ranging from about 0.5% to 20.0% by weight of the composition.

6. The composition as claimed in claim 1, wherein the composition further comprises a penetration enhancer.

7. The composition as claimed in claim 1, wherein the penetration enhancer is selected from isopropyl myristate or oleic acid.

8. A method of treating acne, rosacea, impetigo or a skin disease caused by bacteria, by topical application of the nanoparticulate composition as claimed in claim 1.

* * * * *